(12) United States Patent
Fremy et al.

(10) Patent No.: US 11,897,837 B2
(45) Date of Patent: Feb. 13, 2024

(54) PROCESS FOR THE CO-PRODUCTION OF ALKYL MERCAPTAN AND DIALKYL DISULFIDE FROM ALCOHOL

(71) Applicant: Arkema France, Colombes (FR)

(72) Inventors: Georges Fremy, Lacq (FR); Jean-Michel Raymond, Cauneille (FR); Eric Lamant, Lacq (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 17/740,655

(22) Filed: May 10, 2022

(65) Prior Publication Data
US 2022/0363631 A1 Nov. 17, 2022

(30) Foreign Application Priority Data
May 11, 2021 (FR) ...................................... 2104977

(51) Int. Cl.
C07C 319/24 (2006.01)
C07C 319/28 (2006.01)
C07C 319/08 (2006.01)

(52) U.S. Cl.
CPC .......... C07C 319/24 (2013.01); C07C 319/08 (2013.01); C07C 319/28 (2013.01)

(58) Field of Classification Search
CPC .... C07C 319/08; C07C 319/24; C07C 319/28
See application file for complete search history.

(56) References Cited

U.S. PATENT DOCUMENTS 4,665,242 A 5/1987 Boulinguiez et al.
6,294,699 B1 * 9/2001 Refvik ................. C07C 319/24
568/21

(Continued)

FOREIGN PATENT DOCUMENTS

EP 0171092 A2 2/1986
EP 0171312 A1 2/1986
(Continued)

OTHER PUBLICATIONS

French Search Report and Written Opinion for French Application No. 2104977, dated Dec. 2, 2021, 7 pages.

Primary Examiner — Rosalynd A Keys
(74) Attorney, Agent, or Firm — RatnerPrestia

(57) ABSTRACT

The invention relates to a process for the co-production of alkyl mercaptan and of dialkyl disulfide, comprising the following successive steps:

a) reaction of a $C_1$-$C_4$ alcohol in the presence of hydrogen sulfide ($H_2S$) to form a stream (M) comprising an alkyl mercaptan, water, and possibly unreacted hydrogen sulfide, b) purification of the stream (M) to obtain a stream (N) enriched in alkyl mercaptan, c) recovery of a first portion of the stream (N) including the alkyl mercaptan purified in step b), d) oxidation with sulfur of the second portion of the stream (N) of alkyl mercaptan, to form a stream (O) comprising a dialkyl disulfide, hydrogen sulfide, and possibly unreacted alkyl mercaptan, e) purification of the stream (O) to separate, on the one hand, the enriched dialkyl disulfide and, on the other hand, the hydrogen sulfide and possibly the alkyl mercaptan that has not reacted in step d), f) recycling of the hydrogen sulfide and possibly of the alkyl mercaptan isolated in step e) into the stream (M) obtained from step a), g) recovery of the dialkyl disulfide isolated in step e).

10 Claims, 1 Drawing Sheet

(56) References Cited

U.S. PATENT DOCUMENTS

| | | |
|---|---|---|
| 6,743,951 B2 | 6/2004 | Fremy |
| 8,791,292 B2 | 7/2014 | Forquy et al. |
| 10,550,077 B2 | 2/2020 | Fremy et al. |
| 11,104,642 B2 | 8/2021 | Fremy et al. |
| 2008/0262270 A1 | 10/2008 | Barth et al. |
| 2011/0172138 A1* | 7/2011 | Forquy ................ C07C 319/14 568/21 |
| 2017/0144966 A1* | 5/2017 | Fremy .................... C01B 32/75 |

FOREIGN PATENT DOCUMENTS

| | | |
|---|---|---|
| EP | 0976726 A1 | 2/2000 |
| FR | 2935142 A1 | 2/2010 |
| WO | 2016001553 A1 | 1/2016 |
| WO | 2016001554 A1 | 1/2016 |

* cited by examiner

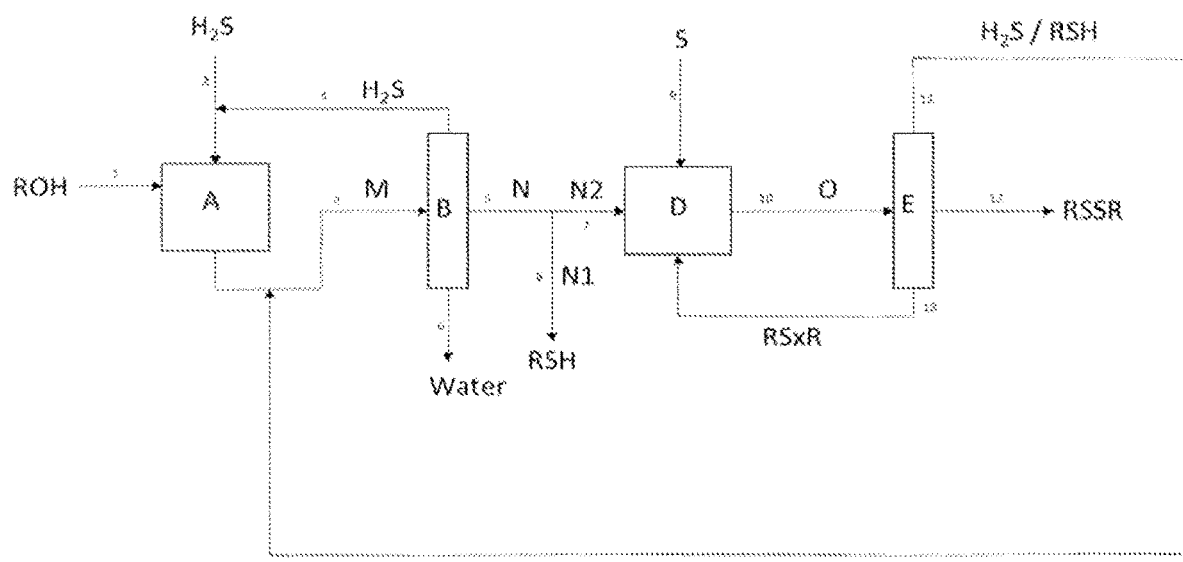

PROCESS FOR THE CO-PRODUCTION OF ALKYL MERCAPTAN AND DIALKYL DISULFIDE FROM ALCOHOL

CROSS-REFERENCE TO RELATED APPLICATIONS

This application claims priority to French Application No. FR2104977, filed May 11, 2021, the disclosure of the application being incorporated herein by reference in its entirety for all purposes.

FIELD OF THE INVENTION

The present invention relates to a process for the co-production of alkyl mercaptan and of dialkyl disulfide from alcohol.

BACKGROUND OF THE INVENTION

Mercaptans are of great interest industrially and are currently in widespread use in the chemical industries, notably as starting materials in the synthesis of more complex organic molecules. For example, methyl mercaptan (noted as $CH_3SH$ or MeSH hereinbelow) is used as a starting material in the synthesis of methionine, an essential amino acid for animal nutrition. Methyl mercaptan is also used in the synthesis of dialkyl disulfides, in particular in the synthesis of dimethyl disulfide (noted as DMDS hereinbelow).

Dialkyl disulfides, and notably dimethyl disulfide, are themselves also of great industrial interest and are widely used industrially. For example, and in a non-limiting manner, they are used as catalyst sulfurization additives, notably in the hydrotreatment of petroleum cuts, as anti-coking and anti-CO additives in petroleum feedstocks subjected to steam cracking for the production of ethylene, or as soil fumigation agents in agriculture.

In comparison with other products used in these applications, for instance di-tert-alkyl polysulfides, organic disulfides, and in particular DMDS, have many advantages. For example, DMDS has a high sulfur content (68%) and non-coking degradation products ($CH_4$, $H_2S$). Furthermore, in these applications, DMDS leads to performance qualities that are generally higher than those of the other commercial products usually used, for example di-tert-alkyl polysulfides.

At the present time, it is known how to produce methyl mercaptan via various synthetic routes.

Methyl mercaptan may be produced from methanol ($CH_3OH$) and hydrogen sulfide ($H_2S$) according to reaction (1) below:

$$CH_3OH + H_2S \rightarrow CH_3SH + H_2O \quad (1)$$

It is also possible to prepare methyl mercaptan from carbon monoxide (CO) according to reaction (2) below:

$$CO + 2H_2 + H_2S \rightarrow CH_3SH + H_2O \quad (2)$$

Other processes are described in the literature and combine various reactions such as:

formation of $CS_2$ and $H_2$ from methane and sulfur, according to reaction (3):

$$CH_4 + H_2S + S \rightarrow CS_2 + 3H_2 \quad (3)$$

hydrogenation of $CS_2$, with the hydrogen formed above, according to reaction (4):

$$CS_2 + 3H_2 \rightarrow CH_3SH + H_2S \quad (4)$$

Dimethyl disulfide is conventionally synthesized by oxidation with sulfur according to reaction (5) below:

$$2CH_3SH + S \rightarrow CH_3SSCH_3 + H_2S \quad (5)$$

This oxidation of alkyl mercaptans with sulfur, catalyzed with homogeneous or heterogeneous, organic or mineral basic agents, in batch mode or continuous mode, is accompanied by a formation of hydrogen sulfide and also of dialkyl polysulfides, noted as RSxR with a sulfur rank x of greater than 2 (for example dimethyl polysulfides $CH_3SxCH_3$ in the case of the synthesis of DMDS). Moreover, this synthetic step generally requires a large excess of methyl mercaptan.

Now, in the context of the current ecological considerations, there is at the present time a real need for a process for the synthesis of alkyl mercaptans and of dialkyl disulfides that is more environmentally friendly, while at the same time maintaining high yields.

BRIEF DESCRIPTION OF THE INVENTION

Thus, one subject of the present invention is a process for the co-production of alkyl mercaptan and of dialkyl disulfide, comprising the following successive steps:

a) reaction of a $C_1$-$C_4$ alcohol in the presence of hydrogen sulfide ($H_2S$) to form a stream (M) comprising an alkyl mercaptan, water, and possibly unreacted hydrogen sulfide, b) purification of the stream (M) to obtain a stream (N) enriched in alkyl mercaptan, c) recovery of a first portion of the stream (N) including the alkyl mercaptan purified in step b), d) oxidation with sulfur of the second portion of the stream (N) of alkyl mercaptan, to form a stream (O) comprising a dialkyl disulfide, hydrogen sulfide, and possibly unreacted alkyl mercaptan, e) purification of the stream (O) to separate, on the one hand, the enriched dialkyl disulfide and, on the other hand, the hydrogen sulfide and possibly the alkyl mercaptan that has not reacted in step d), f) recycling of the hydrogen sulfide and possibly of the alkyl mercaptan isolated in step e) into the stream (M) obtained from step a), g) recovery of the dialkyl disulfide isolated in step e).

This process allows the continuous synthesis of alkyl mercaptan and of dialkyl disulfide. This co-production of products makes it possible to reduce the energy cost of the synthesis. This energy saving is a first ecological advantage.

It also enables the production of each product to be modulated according to the demand. For example, the synthesis of alkyl mercaptan may be favoured over that of the dialkyl disulfide. This flexibility in the process is also an advantage. It is also possible, depending on the need, to produce only the alkyl mercaptan, i.e. to stop the process at step c). Similarly, if need be, all of the stream (N) may be engaged in the oxidation step d). This flexibility of the process is a considerable advantage. It enables the production of the products to be adapted according to the needs, in one and the same facility.

Next, this co-production enables the impurities of the final product to be recycled. The alkyl mercaptan which has not reacted during the oxidation reaction with sulfur and the hydrogen sulfide generated during this oxidation step are recycled into the alkyl mercaptan synthesis. These impurities are usually incinerated, leading to the formation of sulfur oxides ($SO_2$), which are potentially responsible for acid rain. At the present time, these discharges are no longer tolerated. Now, the recycling of all of these light impurities avoids their incineration. The recycling step f) according to the invention thus allows recycling of the hydrogen sulfide on a closed facility. As hydrogen sulfide is a toxic gas, closed recycling makes it possible to limit the handling of this gas, and thereby to limit the accidents.

It would also be possible to separate the hydrogen sulfide from the alkyl mercaptan to economically exploit these impurities. However, this separation is very difficult, requiring distillation apparatus equipped with a very tall column. As a result, this separation is highly energy-intensive. Thus, the recycling of these two impurities into the same stream (i.e. not separated) to be incorporated into an already-existing purification step of the synthetic process is a solution that is simple and very advantageous in energy terms; what is more, the oxidation step with sulfur generally requires a very large excess of alkyl mercaptan.

This recycling is incorporated into a purification step that is essential to the synthetic process. This recycling is thus simple to perform and inexpensive in energy terms. It does not require an additional step in the synthetic process.

Finally, these impurities, which are compounds from the first synthetic step: reagent for the hydrogen sulfide and product for the alkyl mercaptan, enrich this first step of the process, leading to a reduction in the consumption of starting materials.

As regards the reaction, the claimed process covers the following two reactions:

$$ROH + H_2S \rightarrow RSH + H_2O$$

$$2RSH + S \rightarrow RSSR + H_2S$$

These reactions may be simplified the following manner, when the hydrogen sulfide is recycled into the first step:

$$2ROH + H_2S + S \rightarrow RSSR + 2H_2O$$

BRIEF DESCRIPTION OF THE FIGURE

The FIGURE is a scheme of the device performing the claimed process.

DETAILED DESCRIPTION OF THE INVENTION

Other characteristics, aspects, objects and advantages of the present invention will emerge even more clearly on reading the description that follows.

It is pointed out that the expressions "from . . . to . . . " and "between . . . and . . . " used in the present description should be understood as including each of the limits mentioned.

The process according to the invention comprises the seven abovementioned consecutive steps: steps a) to g). This process may include intermediate purification steps.
Step a)—Reaction:

In step a), a $C_1$-$C_4$ alcohol is reacted with hydrogen sulfide to form a stream (M) comprising a $C_1$-$C_4$ alkyl mercaptan, water, possibly unreacted hydrogen sulfide and possibly sulfur-based by-products.

The $C_1$-$C_4$ alcohol according to the invention is chosen from methanol, ethanol, n-propanol, isopropanol, n-butanol, sec-butanol and tert-butanol. Preferably, the alcohol is methanol, ethanol, n-propanol or n-butanol, preferably methanol.

The alcohol and the hydrogen sulfide may be introduced separately into the reactor. It is also possible to make a premix of these reagents.

Prior to step a), a gas stream of the hydrogen sulfide and alcohol reagents may be prepared as follows. Liquid alcohol is injected into gaseous hydrogen sulfide. This injection enables the alcohol to be partially or totally vapourized. The mixture of hydrogen sulfide and alcohol can then be totally vapourized, if necessary, so as to obtain a totally gaseous stream.

Thus, a gas stream of the mixture of hydrogen sulfide and alcohol, preferably prepared as above, is introduced into a reactor. It is also possible to introduce the alcohol and the hydrogen sulfide into the reactor, each in gaseous form.

Said reactor may be isothermal or adiabatic, with plates, multi-tubular or with a fixed bed. An adiabatic reactor is preferably chosen.

The reaction temperature may be between 200° C. and 500° C., preferably between 200° C. and 400° C. Preferably, the reaction temperature is between 200° C. and 360° C. Above this temperature, the catalyst may be physically damaged (notably by sintering and coking).

The pressure may be between 1 and 40 bar absolute.

The hydrogen sulfide/alcohol mole ratio may be between 0.1 and 100, preferably between 1 and 50, and even more preferentially between 1 and 20. Hydrogen sulfide is preferably in excess relative to the alcohol.

The reactor may contain a catalyst for the alkyl mercaptan formation reaction, preferably in the gas phase. Among the catalysts that may be used, mention may be made of:
   alumina-based catalysts;
   thorium dioxide $ThO_2$, preferably deposited on a silicate support;
   catalysts based on cadmium sulfide, preferably on an alumina support;
   catalysts based on the following oxides: MgO, $ZrO_2$, $TiO_2$ rutile (R) and anatase (A), $CeO_2$, and $\gamma$-$Al_2O_3$;
   catalysts based on metal oxides, preferably doped with alkali metals (Li, Na, K, Rb, Cs) and optionally supported on $SiO_2$, $Al_2O_3$ or $Nb_2O_5$;
   catalysts based on alkali metal carbonates;
   catalysts based on alkali metal salts with certain acids of transition metals (Cr, Mo, W, Ni), impregnated on $\gamma$-alumina or other metal oxides;
   potassium tungstate on alumina $K_2WO_4$/$Al_2O_3$.

Preferably, the catalysts are alkali metal oxides impregnated on alumina, and even more preferentially sodium or potassium oxide on alumina of gamma type.

A stream (M) is thus obtained comprising alkyl mercaptan, water, possibly unreacted hydrogen sulfide and sulfur-based by-products.
Additional Condensation Step:

The process according to the invention may comprise at least one step of condensation of the stream (M).

The stream (M) obtained from step a) may be condensed by means of any conventional technique, preferably using one or more condensers or economizers. Preferably, the stream (M) is condensed at a temperature of between 20° C. and 70° C., for example between 30° C. and 60° C.
Step b)—Purification:

The process according to the invention comprises at least one step of purification of the stream (M).

Preferably, in step b), said at least one purification step corresponds to at least one step of phase separation, preferably by decantation, and/or to at least one distillation step. Step b) may notably correspond to one or more phase separation steps, for example one or two decantation steps, and/or one or more distillation steps, for example one or two distillation steps.

Preferably, step b) makes it possible, via one or more purification steps, to remove from the stream (M) the water, the unreacted hydrogen sulfide and/or the sulfur-based by-products that may be present in the stream (M). In particular, after step b), a stream enriched in alkyl mercaptan is obtained.

Preferentially, step b) comprises at least one step of separating out the $H_2S$, in particular by distillation. Preferably, step b) comprises at least one decantation step and at least one distillation step, these two steps enabling the $H_2S$ to be separated from the stream (M). Said decantation and/or distillation steps may be performed under the conditions described below for steps b1) and b2). The purification step b) may be performed via any conventional technique, and in particular by one of the steps b1) and/or b2), preferably by the successive steps b1) to b4) as described below.

Step b1—Separation:

The separation step b1), preferably by decantation, produces:
- a gas stream (M1) comprising unreacted hydrogen sulfide; and
- an organic stream (M2) comprising alkyl mercaptan, possibly water, possibly unreacted hydrogen sulfide and possibly sulfur-based by-products, and
- an aqueous stream (M3).

Preferably, the stream (M) is separated at a temperature of between 20° C. and 70° C., preferably between 30° C. and 60° C. The pressure may be between 1 and 40 bar absolute.

The stream (M2) obtained may notably be in gaseous form or in liquid form. When the stream (M2) is in gaseous form, the streams (M1) and (M2) may be combined.

In particular, the aqueous stream (M3), preferably in liquid form, comprises at least 50%, preferably at least 70%, more preferentially at least 90% by weight of water, relative to the total weight of the water present in the stream (M). The aqueous stream (M3) may thus be sent into a degasser. The degassed aqueous stream may then be sent for waste water treatment.

The gas stream (M1) may be recycled into the reactor feed for step a). In this case, purging of this stream (M1) may be performed so as to avoid the accumulation of inert matter and/or impurities in this recycling loop. Examples of inert matter and/or impurities that may be mentioned include: gaseous alkanes, CO, $CO_2$, $H_2$ and $N_2$. The gas stream resulting from this purging is called E1. When the streams (M1) and (M2) are combined, the same type of purging may be performed so as to obtain a gas stream called E2.

According to one embodiment, the gas streams E1 or E2 are sent for incineration.

According to another embodiment, the gas streams E1 or E2 may be sent into an alcohol absorption column, the alcohol being the one chosen as reagent, so as to recover the sulfur-based compounds such as the hydrogen sulfide and/or the alkyl mercaptan which they comprise, by means of gas-liquid (alcohol) absorption.

Step b2—Removal of the Hydrogen Sulfide by Distillation

The stream (M) or (M2) may undergo distillation so as to obtain:
- a stream (M4) comprising hydrogen sulfide, preferably at the top of the column; and
- a stream (M5) comprising alkyl mercaptan, possibly water and possibly sulfur-based by-products, preferably at the bottom of the column.

During the distillation, the pressure may be between 0.05 and 40 bar absolute, preferably between 1 and 25 bar absolute and/or the temperature may be between −60° C. and +60° C., preferably between 10 and 50° C., at the top of the column; and between +20° C. and +200° C., preferably between 20° C. and 100° C., at the bottom of the column.

The stream (M4) comprising the hydrogen sulfide may be recovered at the top of the column, and optionally recycled into the reactor feed for step a).

In particular, said distillation of step b2) makes it possible to remove the hydrogen sulfide from the stream (M) or from the stream (M2) (it is possible that traces of hydrogen sulfide are still present in the stream (M5)).

Step b3—Optional Removal of the Sulfur-Based By-Products by Distillation:

Distillation of the stream (M2) or of the stream (M5) may be performed so as to obtain:
- a stream (M6) comprising alkyl mercaptan and possibly water, preferably at the top of the column; and
- a stream (M7) which may comprise the sulfur-based by-products, preferably at the bottom of the column.

During the distillation, the pressure may be between 1 and 40 bar absolute, and/or the temperature may be between +20° C. and +100° C., at the top of the column, and between +40° C. and +200° C. at the bottom of the column.

In particular, said distillation of step b3) makes it possible to remove, when they are present, the sulfur-based by-products remaining in the stream (M2) or (M5) (it is possible that traces of the sulfur-based by-products are still present in the stream (M6)).

Step b4—Optional Separation of the Alkyl Mercaptan and of the Traces of Water:

The stream (M2) or the stream (M5) or the stream (M6) may undergo an additional purification step directed towards removing the remaining water. Prior to this step b4), the stream (M2) or the stream (M5) or the stream (M6) may be cooled to a temperature as low as possible, to maximize the water removal. Preferably, the stream (M2) or the stream (M5) or the stream (M6) is cooled to a temperature of between 20° C. and 70° C., for example between 30° C. and 60° C.

This cooling makes it possible to maximize the separation of the water that is potentially still present in the stream, during step b4). When the alkyl mercaptan is methyl mercaptan, a temperature strictly greater than 16° C. is maintained to prevent the formation of solid methyl mercaptan hydrates.

Separation of the alkyl mercaptan and of the remaining water can then be performed, preferably by decantation, so as to obtain:
- a stream (M8) comprising the alkyl mercaptan, preferably in liquid form;
- a stream (M9) comprising water, preferably in liquid form.

In particular, in step b4), the stream (M9) comprises at least 50% by weight, preferably at least 70%, more preferentially at least 90% by weight of water, relative to the total weight of the water present in the stream (N).

In the separation step b4), it is possible to recover the gas phase thus separated from the streams (M8) and (M9), which are both in liquid form. This gas stream is called E3.

According to one embodiment, the gas stream E3 is incinerated.

According to another embodiment, the gas stream E3 may be sent into an alcohol absorption column, the alcohol corresponding to the alcohol used as reagent, so as to recover the sulfur-based compounds such as the hydrogen sulfide and/or the alkyl mercaptan which they comprise, by means of gas-liquid extraction.

Additional Step of Drying of the Stream

The stream (M2) or the stream (M5) or the stream (M6) or the stream (M8) obtained may then be dried.

The drying may take place on molecular sieves, on $MgSO_4$, with $H_2SO_4$, on $CaCl_2$ or by azeotropic distillation, the latter being possible only when the alcohol used as reagent is methanol.

The stream recovered on conclusion of step b) is noted (N).

Step c)—Recovery of the Alkyl Mercaptan:

The process according to the invention then comprises a step of recovery of the alkyl mercaptan. A portion of the stream (N), noted (N1), is recovered for optional engagement in another process. The second portion of the stream (N), noted (N2), is, itself, engaged in the next step of the process according to the invention: step d).

Step d)—Oxidation:

In step d), a portion of the alkyl mercaptan (N2) obtained on conclusion of step c) is reacted, by oxidation with sulfur to form a stream (O) comprising dialkyl disulfide, hydrogen sulfide, possibly unreacted alkyl mercaptan, and possibly dialkyl polysulfides.

This step is described, for example, in patent application EP 0 976 726. For example, step d) may be performed at elevated temperature and under pressure, for example between 20 and 200° C., preferably between 20 and 100° C., and the pressure between 2 and 30 bar absolute, preferably between 2 and 15 bar absolute, typically, for example, at about 70° C., under about 6 bar in the case of oxidation with sulfur of methyl mercaptan.

The oxidation reaction d) is performed in a reactor, which may contain a catalyst. A basic catalyst is preferably used. This basic catalyst may be homogeneous, two-phase or heterogeneous (solid). When the catalyst is homogeneous, i.e. soluble in the mercaptan, amines, amidines and guanidines are preferred. When the basic catalyst forms a two-phase aqueous phase, all water-soluble bases, such as sodium hydroxide, potassium hydroxide, and alkali metal, alkaline-earth metal or ammonium hydroxides are preferred. When the base envisaged is a solid, any solid having a basic nature may be envisaged, such as MgO, CaO, alumina or any other support (silica, zirconias, titanium oxides, hydrotalcites, hydroxyapatites, etc.) optionally doped with alkali metal or alkaline-earth metal oxides, or optionally doped zeolites. Preferably, the heterogeneous basic catalysts are basic ion-exchange resins; more preferably, the heterogeneous catalyst is the Amberlyst® A21 resin sold by the company DuPont.

The alkyl mercaptan/sulfur mole ratio of the oxidation step d) may be between 0.1 and 100, preferably between 1 and 50, and more preferentially between 1 and 20.

This oxidation step may make it possible to form a gas stream (O12) comprising hydrogen sulfide and possibly unreacted alkyl mercaptan and a liquid stream (O11) comprising the dialkyl disulfide, and possibly residual dialkyl polysulfides.

Additional Degassing Step:

The stream (O) or the liquid stream (O11) may then be treated in a degasser so as to remove from the liquid stream the residual gases, such as the hydrogen sulfide or the alkyl mercaptan that may be present, forming the stream (O22). The degassed liquid stream is named (O21).

Additional Step of Retrogradation of the Polysulfides

The liquid stream (O21) obtained from the preceding additional degassing step or the stream (O11) obtained from the oxidation step may undergo a step of retrogradation of the polysulfides with a high sulfur rank to polysulfides with a lower sulfur rank, and ideally to disulfides, so as to convert the residual polysulfides into dialkyl disulfides. The reactor used for this retrogradation step is known as a finisher. It includes an inlet for alkyl mercaptan introduced in excess so as to increase the reaction conversion. This finishing step may make it possible to form a gas stream (O32) comprising hydrogen sulfide and possibly unreacted alkyl mercaptan and a liquid stream (O31) comprising the dialkyl disulfide, and residual dialkyl polysulfides.

Additional Degassing Step:

The liquid stream (O31) may undergo an additional degassing step. The liquid stream (O31) may be treated in a degasser so as to remove the residual gases, such as the hydrogen sulfide and possibly the unreacted alkyl mercaptan, forming the stream (O42). The degassed liquid stream is named (O41).

Step e)—Purification

The process according to the invention includes at least one step of purification of the liquid stream obtained from the oxidation step d). This liquid stream may be the stream (O) obtained directly from the oxidation reaction d) or the streams (O11), (O21), (O31) or (O41) depending on the presence of additional degassing or retrogradation steps. This step makes it possible to separate, on the one hand, the enriched dialkyl disulfide and, on the other hand, the hydrogen sulfide and possibly the alkyl mercaptan that has not reacted in step d). Such a step may notably make it possible to separate:
- the enriched dialkyl disulfide,
- the hydrogen sulfide possibly with the unreacted alkyl mercaptan, and
- impurities such as the heavy products, the volatile compounds, the hydroalkyl disulfides or the mercaptoalkyl alkyl sulfides.

This purification step e) may include one or more distillation steps for isolating the dialkyl disulfide. In particular, said purification step e) may include one or more distillation steps, and optionally one or more basic catalysis steps. In particular, said purification step corresponds to step e1) or e6) as described below.

According to a first embodiment, the purification step e) may be performed via any conventional technique and in particular in one or the successive steps e1) to e4) as described below.

Step e1)—Removal of the $H_2S$ Formed:

The purification step e1), preferably by distillation, produces:
- a gas stream (P12) comprising hydrogen sulfide and possibly unreacted alkyl mercaptan and possibly volatile impurities; and
- a liquid stream (P11) predominantly comprising dialkyl disulfide.

In the distillation, the pressure may be between 0.05 and 15 bar absolute, preferably between 1 and 10 bar absolute. The temperature at the bottom of the column may be between 50 and 300° C., preferably between 50 and 200° C. At the top of the column, the temperature may be between 30 and 200° C., preferably between 30 and 120° C.

Step e2)—Removal of the Heavy Products:

A second distillation of the stream obtained from step d) or of the stream (P11) may then be performed so as to obtain:
- a stream (P22) constituting the column head and predominantly comprising dialkyl disulfide and residual traces of volatile impurities; and
- a stream (P21) constituting the column tail and comprising a mixture of heavy impurities.

The stream of the heavy distillation impurities (P21) may be recycled into the dialkyl disulfide synthesis step, notably into step d) or e1), as defined above. It is possible to equip the recycling pipe with a purge so as to avoid the accumulation of impurities in the process.

Step e3)—Removal of the Hydroalkyl Disulfides by Basic Reaction:

The stream obtained from step d) or the stream (P11) and/or the stream (P22) may be reacted in a reactor including a basic catalyst so as to convert the hydroalkyl disulfides into dialkyl trisulfide according to the following reaction:

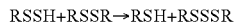

RSSH+RSSR→RSH+RSSSR

The basic catalyst may be of any type known to a person skilled in the art. Said basic catalyst is preferably heterogeneous relative to the reaction medium, so as to facilitate its subsequent separation. Thus, the basic catalyst may be chosen, for example, from anion-exchange resins, such as Amberlyst® A21 from DuPont, basic catalysts in free amine form, aluminas doped with sodium oxide and/or with potassium oxide, magnesium oxide (MgO) and basic zeolites. It is also possible to use the catalysts listed above for the oxidation reaction d). Preferably, the basic catalyst is an anion-exchange resin.

Step e4)—Removal of the Traces of Volatile Compounds:

A third distillation of the stream obtained from step e3) may finally be performed so as to obtain:
- a stream (P31) at the top of the column, comprising the traces of alkyl mercaptan that may be formed in step e3), and
- a stream (P32) constituting the column tail and comprising dialkyl disulfide.

According to a second embodiment, the purification step e) may be performed in steps e5) and e6) as described below.

Step e5)—Removal of the Undesirable Impurities by Basic Reaction:

The liquid stream (O) obtained directly from the oxidation reaction d), or the streams (O11), (O21), (O31) or (O41) depending on the presence of additional degassing or retrogradation steps, may undergo a basic catalysis reaction. Thus, these streams may enter a reactor including a basic catalyst so as to remove the undesirable impurities.

The catalyst used may be the one disclosed for step e3) defined above.

Step e6)—Removal of the Traces of Volatile Compounds and of Heavy Impurities:

A distillation of the stream obtained from step e5) may then be performed so as to obtain:
- a stream at the top of the column comprising hydrogen sulfide and traces of alkyl mercaptan,
- a stream removed in the side position, including dialkyl disulfide, and
- a stream constituting the column tail and comprising the mixture of heavy impurities.

The distillation column used for performing this step may be a column with side withdrawal or a partition column.

If a partition column is used, then the conditions of the column may be the following. The column head temperature may be between 0° C. and 150° C., preferably between 10° C. and 100° C. The column middle temperature may be between 30° C. and 200° C., preferably between 50° C. and 150° C. The column tail temperature may be between 50° C. and 250° C., preferably between 80° C. and 180° C. The pressure inside the column may be between 0.05 bar and 30 bar absolute, preferably between 0.1 and 5 bar absolute. The reflux ratio, defined as being the mass ratio between the liquid reinjected into the top of the column to the distillate containing the light impurities at the top of the column, is between 0 (no reflux) and 100, preferably between 0 and 10.

According to a third embodiment, it is possible to incorporate a distillation column prior to steps e5) and e6), so as to remove the volatile impurities before the basic catalysis step.

Recycling Step f)

The recycling step f) leads the stream to be recycled before the purification step b), which removes the hydrogen sulfide from the stream (M) to be purified, preferably by distillation.

Specifically, the hydrogen sulfide and possibly the alkyl mercaptan recovered during these steps d) and/or e), and optionally the additional steps, is recycled into the stream (M) obtained from step a), i.e. it is injected into the stream (M) so as to undergo the purification step b), which removes the hydrogen sulfide from the stream (M) to be purified, preferably by distillation. Preferably, the recycled stream is reinjected into the medium before step b1) and/or step b2). Thus, the streams (O12), (O22), (O32), (O42), (P12) and (P31) may be pooled as a single stream and reinjected into the stream (M).

A portion or all of the stream may be reinjected into the stream (M). When a portion of the stream is reinjected, the recycling pipe contains a purge, so as to regulate the proportions of the recycled stream. Preferably, all of the stream of hydrogen sulfide, and possibly the alkyl mercaptan that has not reacted in step d), is recycled into the stream (M) obtained from step a).

Recovery Step g)

The dialkyl disulfide is finally recovered.

FIG. 1 shows one embodiment of steps a) to g) of the process according to the invention.

The reaction step a) is performed in a reactor A using alcohol and hydrogen sulfide.

The alcohol stream enters the reactor A via pipe 1. The hydrogen sulfide stream enters the reactor A via pipe 2. The stream M leaving the reactor A via pipe 3 comprises alkyl mercaptan, water, unreacted hydrogen sulfide and possibly sulfur-based by-products.

The purification step b) is performed in a device B, such as a separator. The hydrogen sulfide stream is separated out and removed via a pipe 4, the water is removed via a pipe 6 and the stream N comprising the alkyl mercaptan and possibly sulfur-based by-products leaves the device B via pipe 5.

Pipe 4 is connected to pipe 2 conveying the hydrogen sulfide to the reactor A.

Pipe 5 is divided into a pipe 7 and a pipe 8. Pipe 8 allows recovery of alkyl mercaptan (step c) of the process) and pipe 7 conveys the rest of the stream N to the reactor D.

The oxidation step d) is performed in a reactor D. The sulfur is introduced into the reactor D via pipe 9. The stream O leaving the reactor D via pipe 10 comprises dialkyl disulfide, hydrogen sulfide, unreacted alkyl mercaptan and possibly sulfur-based by-products.

The purification step e) is performed in a device E, such as a distillation column. The stream of hydrogen sulfide and of unreacted alkyl mercaptan is removed at the top of the column via a pipe 11, and the column tail is recycled via a pipe 13 into the reactor D. Pipes 11 and 13 may include a purge. The column middle including the dialkyl disulfide is recovered via a pipe 12.

Pipe 11 recycles the column head comprising the hydrogen sulfide and the unreacted alkyl mercaptan into pipe 3 bringing the stream M to the purification device B.

The examples that follow illustrate the present invention but are not in any way limiting.

Examples

1. Removal of the Sulfur-Based Waste

Two units for the production of DMDS and MeSH were compared. One does not include step f) of recycling the streams after step a). The other is a unit according to the invention and includes this recycling step f). 50000 T/year of MeSH and 50000 T/year of DMDS are produced, i.e. for each of the two products, a production of 151.5 T/day (on a basis of 330 days/year), or 6.3 T/h (on a basis of 24 h/day). Under these conditions, the stream 11 of FIG. 1 contains 2.2 T/h of $H_2S$ and 2.3 T/h of MeSH.

TABLE 1

|  | Emission of $SO_2$ (T/h) | Loss of MeSH yield on the two units combined (%) |
|---|---|---|
| Unit for production of 50 000 tonnes/year of MeSH and 50 000 tonnes/year of DMDS without recycling (comparative - incineration of the stream 11) | 7.3 | 18.3% |
| Unit for co-production of 50 000 tonnes/year of MeSH and 50 000 tonnes/year of DMDS with recycling (invention - recycling of the stream 11) | Negligible | Negligible |

The comparison shows two of the advantages of the process according to the invention. The first advantage is that of avoiding the incineration of sulfur-based products and the release of sulfur oxide into the environment, contributing towards atmospheric pollution. The second is that of improving the yield for the production of MeSH.

The invention claimed is:

1. Process for the co-production of alkyl mercaptan and of dialkyl disulfide, comprising the following successive steps:
   a) reaction of a $C_1$-$C_4$ alcohol in the presence of hydrogen sulfide ($H_2S$) to form a stream (M) comprising an alkyl mercaptan, water, and optionally unreacted hydrogen sulfide,
   b) purification of the stream (M) to obtain a stream (N) enriched in alkyl mercaptan,
   c) recovery of a first portion of the stream (N) including the alkyl mercaptan purified in step b),
   d) oxidation with sulfur of the second portion of the stream (N) of alkyl mercaptan, to form a stream (O) comprising a dialkyl disulfide, hydrogen sulfide, and optionally unreacted alkyl mercaptan,
   e) purification of the stream (O) to separate, on the one hand, an enriched dialkyl disulfide and, on the other hand, the hydrogen sulfide and optionally the alkyl mercaptan that has not reacted in step d),
   f) recycling of the hydrogen sulfide and optionally of the alkyl mercaptan isolated in step e) into the stream (M) obtained from step a),
   g) recovery of the dialkyl disulfide isolated in step e).

2. Process according to claim 1, wherein the recycling step f) leads the stream to be recycled before the purification step b), which removes the hydrogen sulfide from the stream (M) to be purified.

3. Process according to claim 1, wherein all of the stream including the hydrogen sulfide, and optionally the alkyl mercaptan that has not reacted in step d), is recycled into the stream (M) obtained from step a).

4. Process according to claim 1, wherein the $C_1$-$C_4$ alcohol is chosen from methanol, ethanol, n-propanol, iso-propanol, n-butanol, sec-butanol and tert-butanol.

5. Process according to claim 1, wherein the hydrogen sulfide/alcohol mole ratio of step a) is between 0.1 and 100.

6. Process according to claim 1, wherein the reaction of step a) is performed in the presence of a catalyst chosen from catalysts based on alumina, thorium dioxide ($ThO_2$), catalysts based on cadmium sulfide, catalysts based on the following oxides: MgO, $ZrO_2$, $TiO_2$ rutile (R) and anatase (A), $CeO_2$, and γ-$Al_2O_3$, catalysts based on metal oxides, optionally supported on $SiO_2$, $Al_2O_3$ or $Nb_2O_5$, catalysts based on alkali metal carbonates, catalysts based on alkali metal salts with transition metal acids impregnated on γ-alumina where the transition metal is selected from Cr, Mo, W and Ni, potassium tungstate on alumina $K_2WO_4$/$Al_2O_3$.

7. Process according to claim 1, wherein the alkyl mercaptan/sulfur mole ratio of the oxidation step d) is between 0.1 and 100.

8. Process according to claim 1, wherein the reaction temperature of the oxidation step d) is between 20° C. and 200° C. and the pressure is between 2 and 30 bar absolute.

9. Process according to claim 1, wherein the reaction of the oxidation step d) is performed in the presence of a basic catalyst chosen from homogeneous, two-phase or heterogeneous catalysts.

10. Process according to claim 1, wherein the purification step e) includes one or more distillation steps, and optionally one or more basic catalysis steps.

* * * * *